United States Patent [19]

Keller et al.

[11] Patent Number: 5,007,432

[45] Date of Patent: Apr. 16, 1991

[54] RADIATION DETECTION METHOD AND APPARATUS

[75] Inventors: Hans J. Keller, Staefa; Walter A. Kuster, Tuggen, both of Switzerland

[73] Assignee: Eltec Instruments, Inc., Daytona Beach, Fla.

[21] Appl. No.: 377,725

[22] Filed: Jul. 10, 1989

Related U.S. Application Data

[63] Continuation of Ser. No. 42,709, Apr. 27, 1987, abandoned.

[51] Int. Cl.$^5$ .............................................. A61B 5/00
[52] U.S. Cl. .................................... 128/736; 128/738; 374/130
[58] Field of Search ................. 128/736, 738, 664; 374/121, 130-131, 116

[56] References Cited

U.S. PATENT DOCUMENTS

| 2,710,559 | 6/1955 | Heitmuller et al. | 374/130 X |
| 2,813,203 | 11/1957 | Machler | 374/130 X |
| 2,984,747 | 5/1961 | Walker | 374/130 X |
| 3,081,399 | 3/1963 | Schwarz | 374/130 X |
| 3,287,559 | 11/1966 | Barnes | 128/736 X |
| 4,347,854 | 9/1982 | Gosline et al. | 128/736 |
| 4,557,607 | 12/1985 | Busse | 374/130 X |
| 4,602,642 | 7/1986 | O'Hara et al. | 374/129 X |
| 4,635,587 | 1/1987 | Leovardo | 128/738 X |
| 4,693,615 | 9/1987 | Kyriakis | 374/129 |

FOREIGN PATENT DOCUMENTS

| 0490914 | 6/1955 | Italy | 374/130 |
| 0200931 | 11/1984 | Japan | 128/738 |
| WO86/06163 | 10/1986 | PCT Int'l Appl. | 128/736 |

OTHER PUBLICATIONS

"Determination of Fertility . . . Temperature (DST) Measurement", Shaw et al., Fertility and Sterility, 1984.
"Natural Birth Control . . . Solutions", Rao et al., Sadkana, Jun. 1984.
"Computer Assisted Termography . . . Detection", Rao et al., IEEE, 1984, Jul.
"Correlation Study of . . . Thermography", Rao et al., IEEE, Apr. 1982.

*Primary Examiner*—Max Hindenburg
*Attorney, Agent, or Firm*—Duckworth, Allen, Dyer & Doppelt

[57] ABSTRACT

A medical diagnostic method and apparatus employs differential radiation detection apparatus for remotely detecting temperature differentials between a plurlity of areas on the surface of an object having a plurality of lenses which each focus a beam of radiation from a corresponding area of the body onto a radiation detector in such a way that not more than one field of view reaches the detector at any time.

17 Claims, 2 Drawing Sheets

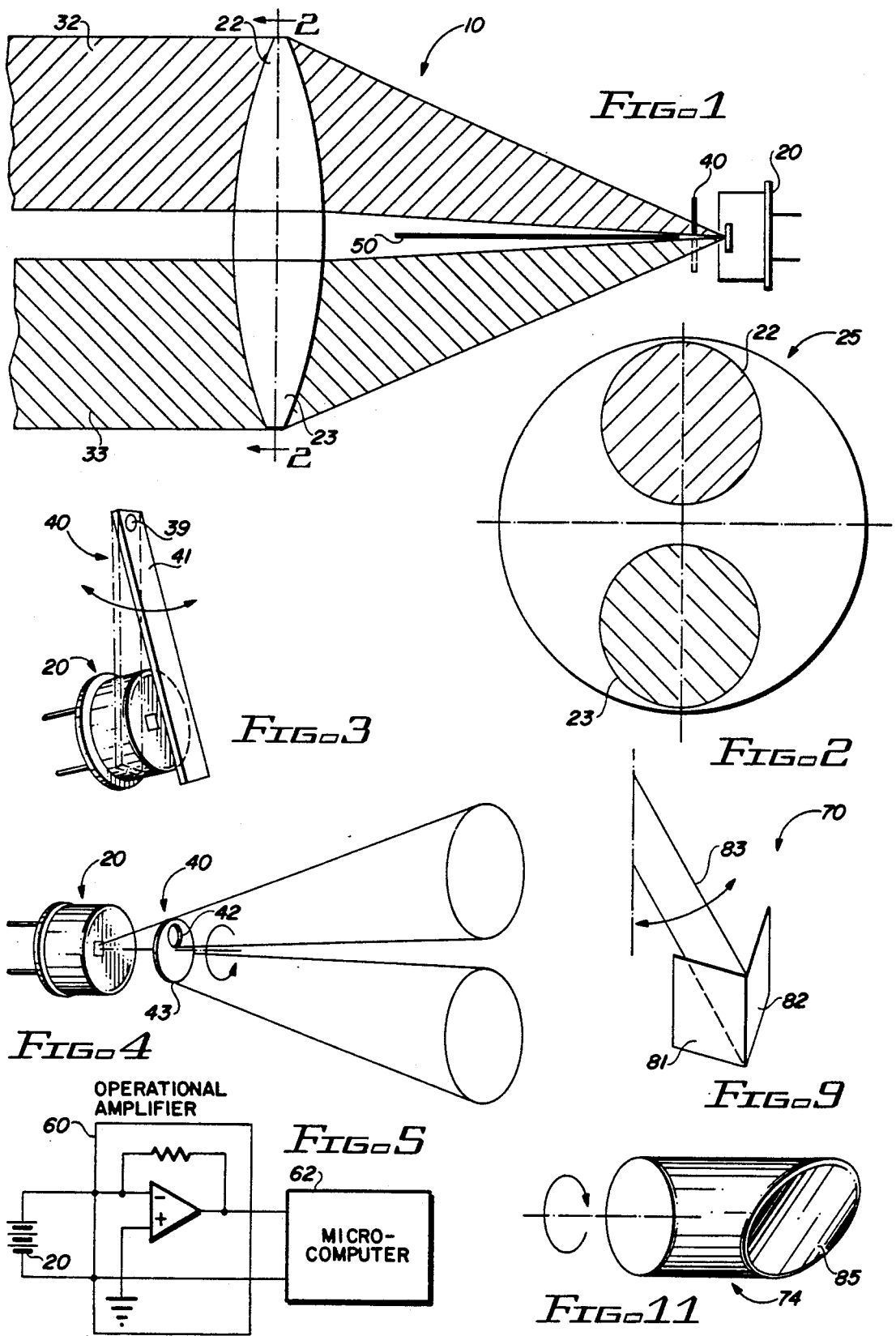

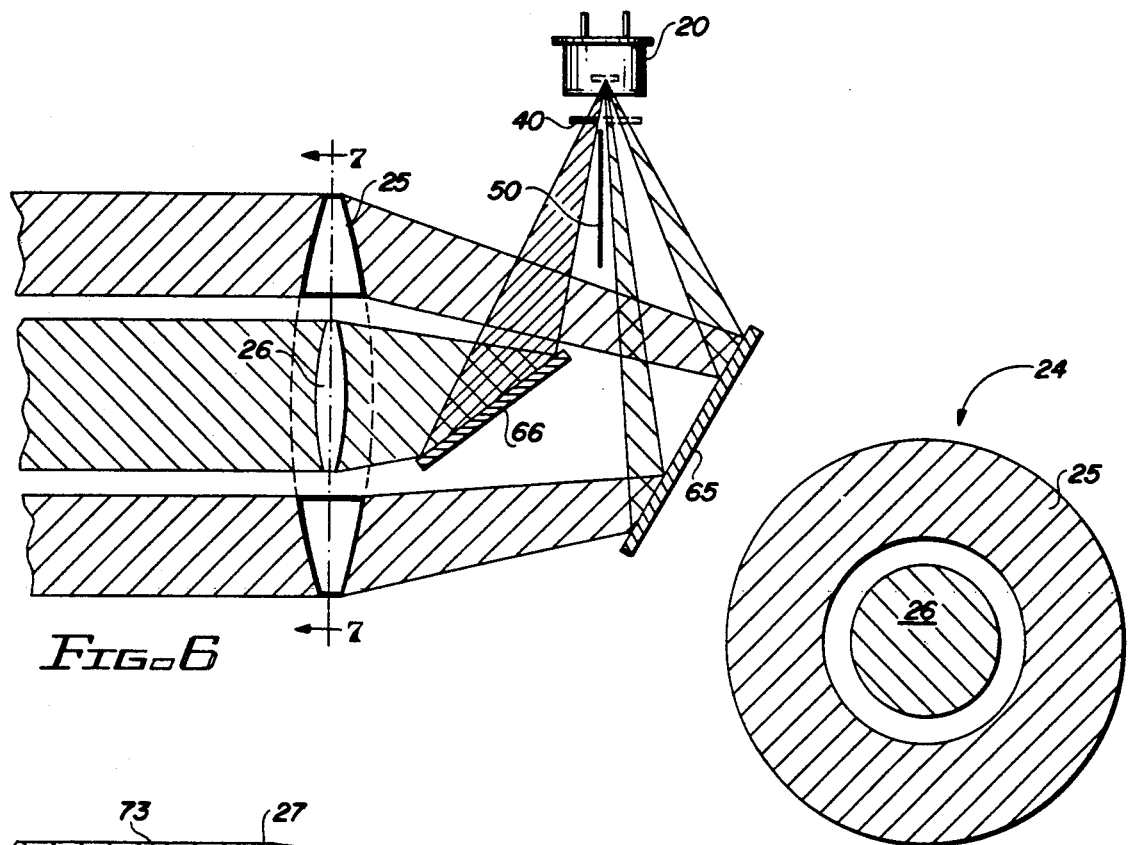
FIG. 6
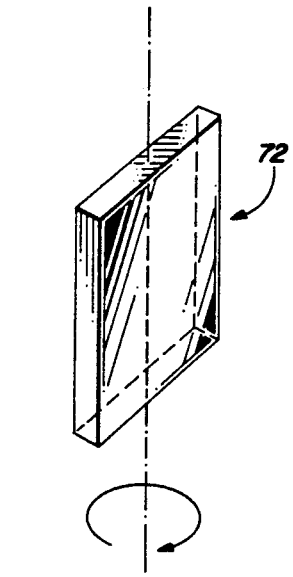
FIG. 7
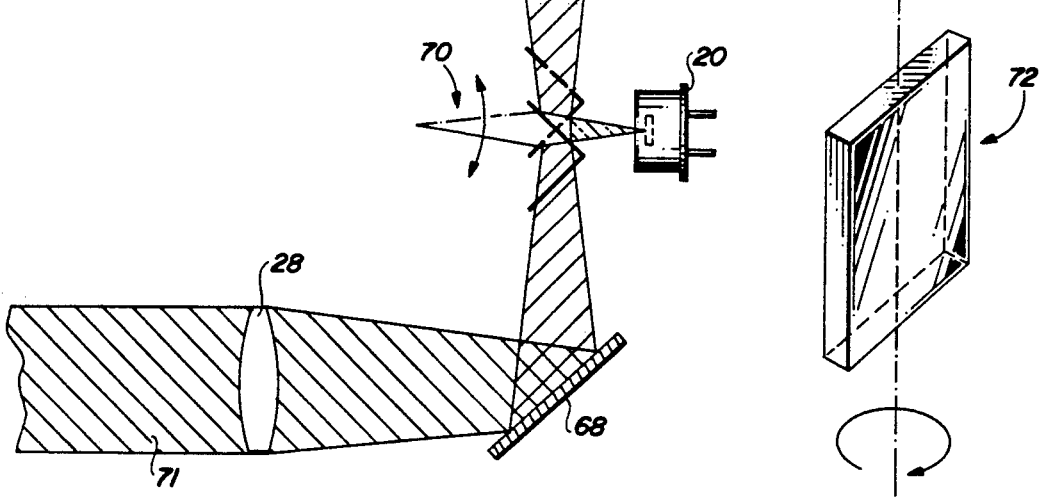
FIG. 8
FIG. 10

RADIATION DETECTION METHOD AND APPARATUS

This is a continuation of application Ser. No. 042,709 filed Apr. 27, 1987, now abandoned.

BACKGROUND OF THE INVENTION

This invention relates to a method and apparatus for medical diagnostic testing by using infrared radiation and, more particularly, to a method and apparatus for determining temperature differences between two or more sites on a body.

Differential skin surface temperature measurement has been useful for determining the ovulation time of women as well as other medical testing. A study by Shah et al, "Determination of Fertility Interval with Ovulation Time Estimation Using Differential Skin Surface Temperature Measurement," *Fertility and Sterility*, May 1984, indicates that the temperature of vascularity sensitive areas can be compared to vascularity insensitive areas to determine the time of ovulation. The vascularity sensitive area measured is the breast and the vascularity insensitive area is the sternum. Just before ovulation the temperature of the vascularity sensitive areas is greater than the vascularity insensitive areas.

Differential temperature measurement may also be useful for detecting soft tissue damage When tissue is inflamed the blood supply to it is increased. This increased blood supply increases the temperature of the tissue. Thus, by comparing the temperature of the damaged tissue to that of the undamaged tissue an injury can be detected. Such information may be useful, for example, in evaluation of so-called "whip-lash" injuries.

The present invention has particular application in determining temperature differences between two or more sites on a human body using infrared detectors. One advantage for using infrared detectors is that a measure of the surface temperature of a site on an object can be determined without contacting the object. However, if only one detector is used to measure the temperature at two or more sites, the probability of measurement inaccuracies due to moving the detector is great. On the other hand, if different detectors are used to measure the temperature at different sites, measuring inaccuracies due to drifts or tolerances between the different detectors is likely. An apparatus which can measure two or more sites on a human body or on other objects without these drawbacks is therefore desirable.

Infrared detectors measure the infrared radiation emitted by a surface. By analyzing the wavelength and intensity of the radiation, the surface temperature can be remotely determined. Detectors used in such systems, for example, pyroelectric infrared detectors, typically have a body of pyroelectric material and electrical output leads. A change in temperature of the pyroelectric material creates a change in polarization and current is produced only as the material experiences a temperature change. When it is at a constant temperature, no current is produced. When radiation is absorbed by the material, an electrical current flows in a circuit connected to the output leads thereby providing an indication of the radiation. Such detectors are not only exposed to the radiation emitted by the surface to be measured, but also to radiation emitted by themselves or their environment. Thus, the measuring accuracy of the system is reduced.

In one attempt to overcome this problem, two detector elements, connected in inverse parallel arrangement have been employed with one of the elements exposed to incident radiation while the other detector element is only exposed to internal or environmental radiation. In another attempt to overcome the accuracy problem, a system with a single detector element has been used together with a chopper which alternately exposes the detector to incident radiation and then to internal radiation only.

Prior patents pertaining to detecting temperatures of an object using radiation detectors include: U.S. Pat. No. 3,722,282 to Loy; U.S. Pat. No. 3,972,598 to Kunz; U.S. Pat. No. 4,268,752 to Herwig et al; U.S. Pat. No. 4,339,748 to Guscott et al; U.S. Pat. No. 4,442,357 to Baker et al; U.S. Pat. No. 4,514,630 to Takahashi; and U.S. Pat. No. 4,514,631 to Guscott.

U.S. Pat. No. 3,722,282 to Loy discloses the use of a modulator device which alternately switches the radiation transmitted to a detector between that emanating from a point in a scene and a reference beam which indicates the mean temperature of the scene. Loy requires a plurality of mirrors or lenses for focusing each beam of radiation onto a detector. U.S. Pat. No. 3,972,598 to Kunz discloses a multifaceted mirror structure which focuses light from a plurality of discrete points onto a single radiation detector. The Guscott and Takahashi patents are similar except that a dual mirror system is utilized for focusing radiation.

The patent to Herwig discloses an apparatus for focusing radiation beams from different directions onto a single detector in which a plurality of planar mirrors initially deflect incoming beams onto a concave mirror. The concave mirror reflects the beams onto a further deflecting mirror which directs the beams to a detector.

The patent to Baker et al discloses a differential radiation detection apparatus for determining the level of liquid in a container by measuring the temperature of the container above and below the level of the liquid. In that patent, the radiation from two points on the same object is reflected by a concave mirror to the detection apparatus. A disadvantage of this system is that the apparatus comprises a pair of thermal radiation detectors.

It is an object of this invention to provide a noncontact temperature sensing system and method for accurately determining a temperature differential on the surface of an object.

It is another object of the present invention to provide a temperature differential measurement system and method which is not prone to environmental effects.

It is still another object of the present invention to avoid temperature differential measuring inaccuracies originating from moving the measuring system.

It is still another object of the present invention to provide a method and apparatus for temperature differential measurement using the same radiation detector to measure the radiation from all points being measured to avoid drifts or tolerances between different detectors.

SUMMARY OF THE INVENTION

The present invention teaches a method and apparatus for detecting a temperature differential on an object with a single radiation detector. In one embodiment, a system is illustrated using lenses for receiving thermal radiation from a plurality of areas on the surface of the object and focusing the radiation onto a detector. The system has a switching shutter mechanism for preventing thermal radiation from more than one area of the object to be received by the detector at any time. In accordance with a preferred embodiment, the radiation detection system repeatedly senses infrared radiation of each of the areas and makes a comparison of the radiation signals for each sample period. Thus, an accurate measurement of temperature differential between areas can be determined. A shield may also be provided to the apparatus to prevent cross-talk between the fields of view.

BRIEF DESCRIPTION OF THE DRAWINGS

The foregoing and other objects, features and advantages of the invention will become more apparent by reference to the accompanying drawings and the following detailed description taken in conjunction with the accompanying drawings in which:

FIG. 1 is a side view of a differential radiometer in accordance with the present invention;

FIG. 2 is a section view 2—2 from FIG. 1;

FIG. 3 illustrates a switching mechanism to be used with a differential radiometer;

FIG. 4 shows another embodiment of a switching mechanism to be used with a differential radiometer;

FIG. 5 is a schematic drawing of a radiation detector with a measuring mechanism;

FIG. 6 is a side view of a differential radiometer having a plurality of concentric lenses in conjunction with mirrors for focusing radiation on a detector;

FIG. 7 is a front view of the lenses in FIG. 6;

FIG. 8 is a differential radiometer which uses a plurality of mirrors and lenses to focus thermal radiation on the detector;

FIG. 9 is a switching mechanism which can be used with a differential radiometer of FIG. 8;

FIG. 10 is a switching mechanism which can be used with a differential radiometer of FIG. 8; and FIG. 11 is a switching mechanism which can be used with a differential radiometer of FIG. 8.

DETAILED DESCRIPTION

Referring now to FIG. 1, a preferred embodiment of the present invention is shown in the form of a differential radiometer 10 having first and second lenses 22 and 23 which each receive thermal radiation, depicted by the numerals 32 and 33, from corresponding areas of an object (not shown) for focusing the radiation 32 and 33 onto a thermal radiation detector 20. A switching shutter mechanism 40 is provided for alternately interrupting the reception of thermal radiation 32 and 33 by the detector 20 at a predetermined frequency so that the thermal radiation 32 or 33 from not more than one area of the object is received by the detector 20 at any time. Thus, the switching shutter mechanism 40 alternately allows thermal radiation from one area of the object to be measured while blocking thermal radiation from the other areas of the object. A shield 50 may also be provided to prevent cross-talk between the two beams of thermal radiation. FIG. 2 illustrates the two lenses 22 and 23 rigidly contained within a single transparent body 25. The lenses 22 and 23 preferably have the same focal point to direct radiation at a single detector. By combining the lenses 22 and 23 on a common substrate 25, errors from dust and varying angles of view are reduced. The lenses 22 and 23 may also be selected portions of one single lens comprising the body 25. Alternatively, the lenses could be mounted in a common holder similar to a pair of glasses.

Reference is now made to FIG. 3 which shows one form of the switching shutter mechanism 40 having a small, flat plate 41 which pivots about an axis, indicated at 39, normal to the face of the detector 20 so that the plate 41 transversely vacillates between the incoming beams of radiation to alternately allow only one beam of radiation to be received by the detector 20 at any time. FIG. 4 illustrates an alternative form of the switching shutter mechanism 40 using a rotating disc 43 having an off-centered aperture 42 to alternately pass a beam of radiation to be received by the detector 20. The disc 43 rotates about an axis normal to the face of the detector such that radiation received by the detector 20 must first pass through the aperture 42. Thus, as the disc 40 rotates about its axis, the beams of thermal radiation are blocked until the aperture 42 aligns with both the beam and the detector 20.

Although FIG. 4 illustrates an apparatus employing only two radiation beams, it will be appreciated that more than two beams are capable of being sensed by detector 20 by appropriately timing the operation of shutter mechanism 40. Since only one radiation beam can pass through the aperture 42 of the rotating disc 43, the shutter mechanism 40 is capable of employing more than two radiation beams. Accordingly, the illustration of only two beams is not considered to be limiting. Furthermore, while the mechanism 40 has been illustrated as a mechanical shutter, it will be appreciated that an electronic mechanism such as, for example, a liquid crystal device or an electro-optical switching crystal or a microshutter, could be substituted.

Reference is now made to FIG. 5 which illustrates a simplified block diagram of the detector 20 and associated circuit for measuring the temperature of each of the respective areas of the object to be measured. The detector 20 is a pyroelectric detector of a type well known in the art which converts received thermal radiation into an electric potential. The greater the change in temperature between the area being measured and the detector 20 itself, the greater the potential. Since the potential developed by detector 20 is relatively small, an operational amplifier 60, well known in the art, is attached to the detector 20 to amplify the signal from the detector 20. A microcomputer 62, well known in the art, is attached to the operational amplifier 60 for receiving the amplified electric signal and translating it into temperature indicative signals. The microcomputer 62 includes memory means for storing a plurality of the temperature indicative signals which can be subsequently averaged and compared for determining the surface temperatures or surface differential temperatures of the corresponding sites of the object to be measured.

Reference is now made to FIG. 6 which illustrates another embodiment of the present invention. Here, two concentric lenses 25 and 26 are used in conjunction with two corresponding mirrors 65 and 66, respectively, for receiving two beams of incident thermal radiation from two areas on an object and focusing the two beams onto the same detector 20. The focal length of the inner lens 26 is shorter than the focal length of the outer ring shaped lens 25. The mirror 66 which reflects thermal radiation from the inner lens 26 to the detector and the mirror 65 reflects thermal radiation from the outer lens 25 to the detector 20. The mirrors 65 and 66 are positioned so that both beams of radiation are focused on the detector 20. Preferably, the incident angles of the two beams with respect to the detector 20 are different so that the beams can easily be blocked with the switching shutter mechanism 40. Additionally, the mirror 66 which reflects the beam from the inner lens 26 is dimensioned so as not to interfere with the beam from the outer lens 25. A shield 50 can also be provided to prevent cross-talk between the two beams. FIG. 7 is a front or face view of the two lenses 25 and 26. Preferably, the two lenses 25 and 26 are made from the same mold so that both lenses 25 and 26 are contained within a single optical system 24.

Reference is now made to FIG. 8 which shows yet another embodiment of the present invention. Here, two parallel beams 71 and 73 of thermal radiation from two areas of an object to be measured each pass through a corresponding lens 27 and 28 and deflect off corresponding mirrors 67 and 68 and onto a mirrored switching mechanism 70 which alternately deflects each beam onto radiation detector 20. In this embodiment, the detector 20 is positioned on a line equidistant from the two beams. The two beams 71 and 73 of thermal radiation respectively pass through the two lenses 27 and 28 and are inwardly deflected by respective mirrors 67 and 68 at approximately the same inward angle. The mirrored switching mechanism 70 then alternately deflects one of the two beams to the detector 20. The mirrors and lenses are positioned so that the beams focus on the detector 20 when the mechanism 70 appropriately deflects the beams.

FIG. 9 illustrates one form of the mirrored switching mechanism 70 having two mirrored plates 81 and 82 mounted approximately normal to each other and attached to a swinging member 83. As the switching mechanism 70 swings back and forth, it alternately allows one of the two beams of thermal radiation to contact the radiation detector 20. Thus, the swinging of the switching assembly 70 effectively permits only one beam of radiation to be focused on the detector 20 at any time. FIG. 10 illustrates an alternate form of the mechanism 70 using a plate 72 having mirrors on both faces which can be seen to correspond to the mirror faces 81, 82 of the embodiment of FIG. 9. The plate 72 is rotated normal to the paths of the beams of radiation so that one of the beams 71, 73 of radiation alternately is directed onto the detector 20. FIG. 11 illustrates a still further embodiment of the mechanism 70 using an elliptically truncated cylinder 74, having a mirrored elliptical face 85. The cylinder 74 is rotated about its axis such that the beams 71, 73 are alternated deflected toward detector 20.

Although the invention has been disclosed in the context of a medical diagnostic system, it will be apparent that the invention is also applicable in any application requiring temperature differential measurement between displaced sites. Accordingly, the invention is not to be construed as limited to medical applications.

While the principals of the invention have now been made clear in an illustrative embodiment, there will become obvious to those skilled in the art many modifications in structure, materials, components and form used in the practice of the invention and otherwise which are particularly adapted for specific operating requirements without departing from those principals. The appended claims are therefore intended to cover and embrace any such modifications, within the limits only of the true spirit and scope of the invention.

We claim:

1. A medical diagnostic apparatus for detecting the temperature differential between two sites on the surface of a person's body comprising:
   a single thermal radiation detector;
   a plurality of lenses arranged to respectively receive thermal radiation from different sites on the person's body along different optical paths and to focus the received radiation onto the single detector;
   means for alternately interrupting the flow of thermal radiation from the different sites to the detector so that the thermal radiation from not more than one of the sites is received by the detector at any time;
   means for converting the received thermal radiation from each site to corresponding temperature indicative signals;
   means for averaging the temperature indicative signals derived from each corresponding site to determine the surface temperature of each site; and wherein
   the plurality of lenses are concentric and lie in a common plane.

2. The apparatus of claim 1 wherein the lenses are combined on a common substrate.

3. The apparatus of claim 1 wherein the means for interrupting the thermal radiation to the detector comprises a switching shutter mechanism.

4. A medical diagnostic method for remotely determining the temperature of a plurality of sites on the surface of a person's body comprising the steps of:
   providing a single thermal radiation detector;
   providing lens means which respectively receive thermal radiation from different sites on the surface of the person's body and focus the received radiation onto the detector;
   alternately interrupting the flow of thermal radiation to the detector from the different sites so that the thermal radiation from not more than one of the sites is received by the detector at any time;
   converting the received thermal radiation from each site to corresponding temperature indicative signals; and
   averaging the temperature indicative signals derived from each corresponding site to determine the surface temperature of each site.

5. The method of claim 4 further comprising the step of determining the temperature differential between the two sites.

6. An apparatus for detecting the temperatures of a plurality of areas on the surface of an object comprising:
   a thermal radiation detector;
   a plurality of concentric lenses arranged to respectively receive thermal radiation from different areas on the surface of an object;
   a plurality of deflecting mirrors positioned to respectively deflect the radiation from the field of view from each of the lenses onto the detector such that the radiation from the fields of view focus on the detector; and
   means for passing radiation from not more than one field of view to the detector at any time.

7. The apparatus of claim 6 wherein the means for passing radiation from not more than one field of view to the detector at any time comprises a mechanical switching shutter mechanism.

8. The apparatus of claim 6 wherein said lenses are coplanar.

9. The apparatus of claim 8 wherein the lenses are fixed on a common substrate.

10. The apparatus of claim 9 wherein the means for passing radiation from not more than one field of view to the detector at any time comprises a switching shutter mechanism.

11. An apparatus for detecting the temperatures of a plurality of areas on the surface of an object comprising:
 a thermal radiation detector;
 a plurality of lenses arranged to respectively have different fields of view of the object of which the temperature is to be determined;
 a mirror switching mechanism which oscillates at a predetermined frequency; and
 a plurality of deflecting mirrors positioned to respectively deflect the radiation from the fields of view from the lenses onto the mirror switching mechanism which in turn alternately deflects each field of view onto the detector.

12. The apparatus according to claim 11 wherein the radiation detector comprises an infrared pyroelectric detector.

13. The apparatus of claim 11 wherein the detector comprises a differentially connected radiation sensor.

14. The apparatus according to claim 11 further comprising:
 means for repeatedly measuring the temperatures of each of the areas; and
 means for averaging the measured temperatures of each area for determining the surface temperature of each area.

15. An apparatus for detecting the temperatures of a plurality of areas on the surface of an object comprising:
 an infrared radiation detector;
 a plurality of combinations of mirror-lens arrangements for receiving and focusing thermal radiation from different areas onto the detector;
 means for alternately interrupting the thermal radiation from the different areas to said detector at a predetermined frequency so that the thermal radiation from not more than one area of the object is received by the detector at any time; and
 means for averaging the temperature radiation received from each area a number of times and comparing that average with the average for another area.

16. A method for remotely determining the temperatures of a plurality of areas on the surface of an object comprising the steps of:
 providing a thermal radiation detector;
 providing a plurality of lenses which respectively receive thermal radiation from different areas on the surface of the object and focus the radiation onto the detector;
 alternately interrupting the flow of thermal radiation to the detector from the different areas so that the thermal radiation from not more than one area of the object is received by the detector at any time;
 converting the received thermal radiation to a temperature indicative signal; and
 averaging a plurality of the temperature indicative signals for determining the average surface temperature of each area, and comparing that average with the average for another area.

17. A method for detecting the occurrence of ovulation in a woman's menstrual cycle, comprising the steps of:
 providing a thermal radiation detector;
 providing at least two concentrically arranged lenses lying in a common plane;
 focusing one of the two lenses on a hormonally sensitive area of the body of the woman;
 focusing another one of the two lenses on a hormonally insensitive area of the body of a woman;
 positioning each of the two lenses such that thermal radiation from each area is focused onto the thermal radiation detector;
 alternately blocking the radiation from each of the at least two lenses so that only radiation from one of the areas is received by the detector at any time;
 converting the received radiation to temperature indicative signals;
 comparing the signals corresponding to one of the areas to the signals corresponding to the other of the areas;
 providing an indication of ovulation when the signals are representative of different temperatures at each of the areas; and
 averaging a plurality of the temperature indicative signals for determining the average surface temperature of each area, and comparing that average with the average for another area.

* * * * *